(12) United States Patent
Yano

(10) Patent No.: US 11,963,280 B2
(45) Date of Patent: Apr. 16, 2024

(54) ILLUMINATION LIGHT ADJUSTING SYSTEM, ILLUMINATION LIGHT ADJUSTING METHOD, AND NON-TRANSITORY COMPUTER-READABLE STORAGE MEDIUM

(71) Applicants: IRIS COMMUNICATION KABUSHIKI KAISHA, Tokyo (JP); NICO CORPORATION, Tokyo (JP)

(72) Inventor: Masafumi Yano, Miyagi (JP)

(73) Assignees: IRIS COMMUNICATION KABUSHIKI KAISHA, Tokyo (JP); NICO CORPORATION, Tokyo (JP)

( * ) Notice: Subject to any disclaimer, the term of this patent is extended or adjusted under 35 U.S.C. 154(b) by 440 days.

(21) Appl. No.: 17/109,198

(22) Filed: Dec. 2, 2020

(65) Prior Publication Data

US 2021/0084731 A1     Mar. 18, 2021

Related U.S. Application Data

(63) Continuation-in-part of application No. PCT/JP2019/013580, filed on Mar. 28, 2019.

(30) Foreign Application Priority Data

Jun. 19, 2018  (JP) .................................. 2018-115719

(51) Int. Cl.
*H05B 47/105* (2020.01)
*G06V 10/141* (2022.01)
(Continued)

(52) U.S. Cl.
CPC ......... *H05B 47/105* (2020.01); *G06V 10/141* (2022.01); *G06V 10/56* (2022.01);
(Continued)

(58) Field of Classification Search
CPC .. H05B 47/105; H05B 47/115; H05B 47/125; H05B 47/135; H05B 47/155; H05B 47/175
See application file for complete search history.

(56) References Cited

U.S. PATENT DOCUMENTS 4,663,657 A * 5/1987 Nagasaki ................. A61B 1/05
348/70
2009/0026978 A1 * 1/2009 Robinson ............. H05B 47/175
315/294
(Continued)

FOREIGN PATENT DOCUMENTS

JP  2008-181874 A    8/2008
JP  2010-262806 A    11/2010
(Continued)

OTHER PUBLICATIONS

Sep. 21, 2021 Office Action issued in Japanese Patent Application No. 2020-525276.
(Continued)

*Primary Examiner* — Tung X Le
(74) *Attorney, Agent, or Firm* — Oliff PLC

(57) ABSTRACT

An illumination light adjusting system according to the present disclosures includes a color vision characteristics storage configured to store color vision characteristics of a user, and a wavelength characteristics changing unit configured to change wavelength characteristics of illumination light based on the color vision characteristics stored in the color vision characteristics storage.

24 Claims, 9 Drawing Sheets

(51) Int. Cl.
*G06V 10/56* (2022.01)
*G06V 40/16* (2022.01)
*H05B 47/125* (2020.01)

(52) U.S. Cl.
CPC ............ *G06V 40/16* (2022.01); *G06V 40/172* (2022.01); *H05B 47/125* (2020.01)

(56) References Cited

U.S. PATENT DOCUMENTS

| | | | | |
|---|---|---|---|---|
| 2011/0116046 | A1* | 5/2011 | Haeri | A61B 3/0008 |
| | | | | 351/221 |
| 2014/0015762 | A1* | 1/2014 | Weng | G07F 9/0235 |
| | | | | 345/173 |
| 2015/0048924 | A1* | 2/2015 | Feldstein | G07C 9/27 |
| | | | | 340/5.51 |
| 2015/0115833 | A1* | 4/2015 | Kwon | H05B 45/20 |
| | | | | 315/294 |
| 2015/0248228 | A1* | 9/2015 | Seuntiens | H05B 47/155 |
| | | | | 715/765 |
| 2017/0265277 | A1 | 9/2017 | Nolan et al. | |
| 2018/0129050 | A1 | 5/2018 | Hayashi et al. | |
| 2018/0332684 | A1* | 11/2018 | Lee | H05B 47/155 |
| 2019/0124745 | A1* | 4/2019 | Mason | G06F 18/231 |
| 2020/0102092 | A1* | 4/2020 | Heine | H05B 47/11 |

FOREIGN PATENT DOCUMENTS

| | | |
|---|---|---|
| JP | 2013-041718 A | 2/2013 |
| JP | 2017-527087 A | 9/2017 |
| KR | 10-2016-0113861 A | 10/2016 |
| WO | 2017/123702 A1 | 7/2017 |

OTHER PUBLICATIONS

Dec. 22, 2020 International Preliminary Report on Patentability issued in International Patent Application No. PCT/JP2019/013580.
May 21, 2019 International Search Report issued in International Patent Application No. PCT/JP2019/013580.
Jan. 26, 2022 Search Report isssued in European Patent Application No. 19822462.8.

* cited by examiner

ILLUMINATION LIGHT ADJUSTING SYSTEM, ILLUMINATION LIGHT ADJUSTING METHOD, AND NON-TRANSITORY COMPUTER-READABLE STORAGE MEDIUM

CROSS-REFERENCE TO RELATED APPLICATION

This is a Continuation-in-Part of International Application No. PCT/JP2019/013580 filed on Mar. 28, 2019, which claims priority from Japanese Patent Application No. 2018-115719 filed on Jun. 19, 2018. The entire disclosures of the prior applications are incorporated herein by reference.

TECHNICAL FIELD

The present disclosure relates to an illumination light adjusting system, an illumination light adjusting method, and a non-transitory computer-readable storage medium storing computer-readable instructions regarding the illumination light adjusting method.

BACKGROUND

As impairment of a human visual sense, color vision deficiency is known. Examples of the color vision deficiency may include, but are not limited to, color blindness and color weakness which are decreased abilities to sense light of a specific wavelength band, and photo-allergy that a sufferer feels dazzled by the light. Such color vision deficiencies are caused by higher or lower light sensitivity of three types of cone cells (i.e., S cone cell, M cone cell, and L cone cell) on a retina of the sufferer. The S cone cell, the M cone cell, and the L cone cell are sensitive to blue, green, and red lights, respectively. As a method for correcting the color vision deficiency, a method of using an optical element (e.g., a color lens) of which light transmission characteristics are adjusted for a sufferer is known. The color vision deficiency of the sufferer may be corrected when the sufferer wears glasses having the color lens of which the light transmission characteristics are adjusted. Alternatively, an environment suitable for the sufferer may be obtained by installing indoors an illumination device configured to change the wavelength characteristics of illumination light and changing the wavelength characteristics of the illumination light according to the color vision characteristics and preferences of the sufferer.

Heretofore, there has been known an illumination system configured to change the wavelength characteristics of illumination light. The known illumination system includes a light source configured to change luminance of emitted light in accordance with a driving current, and an optical element configured to change a wavelength of transmitted light in accordance with a driving voltage. By changing the driving current and the driving voltage, a user may change the brightness and the wavelength characteristics of the illumination light emitted from the light source and transmitted through the optical element according to the user's preference.

SUMMARY

However, in the known illumination system, the user arbitrarily designates the driving current for the light source and the driving voltage for the optical element to change the wavelength characteristics of the illumination light. Therefore, when the user has the color blindness or the color weakness, the user's preferred wavelength characteristics might not match the wavelength characteristics suitable for the color vision characteristics of the user. In this case, the user might be unable to recognize color differences since the arbitrarily set wavelength characteristics of the illumination light are not suitable for the color vision characteristics of the user. Further, in the known illumination system, the user manually changes the wavelength characteristics of the illumination lights. Hence, when there are a plurality of environments in which the wavelength characteristics of the illumination light are changeable (e.g., when the wavelength characteristics of illumination light in a living room, a bedroom, and a dining room, and the wavelength characteristics of light from televisions and PC monitors are changeable), it is difficult to match the wavelength characteristics of all the illumination lights with each other.

According to aspects of the present disclosure, there is provided an illumination light adjusting system including a color vision characteristics storage configured to store color vision characteristics of a user, and a wavelength characteristics changing unit configured to change a wavelength characteristics of an illumination light based on the color vision characteristics stored in the color vision characteristics storage.

According to aspects of the present disclosure, there is provided an illumination light adjusting method including storing color vision characteristics of a user, and changing a wavelength characteristics of an illumination light based on the color vision characteristics stored in the color vision characteristics storage.

According to aspects of the present disclosure, there is provided a non-transitory computer-readable storage medium storing computer-readable instructions configured to, when executed by a computer, cause the computer to perform the illumination light adjusting method.

Brief Description of the Accompanying Drawings

Figure 7:
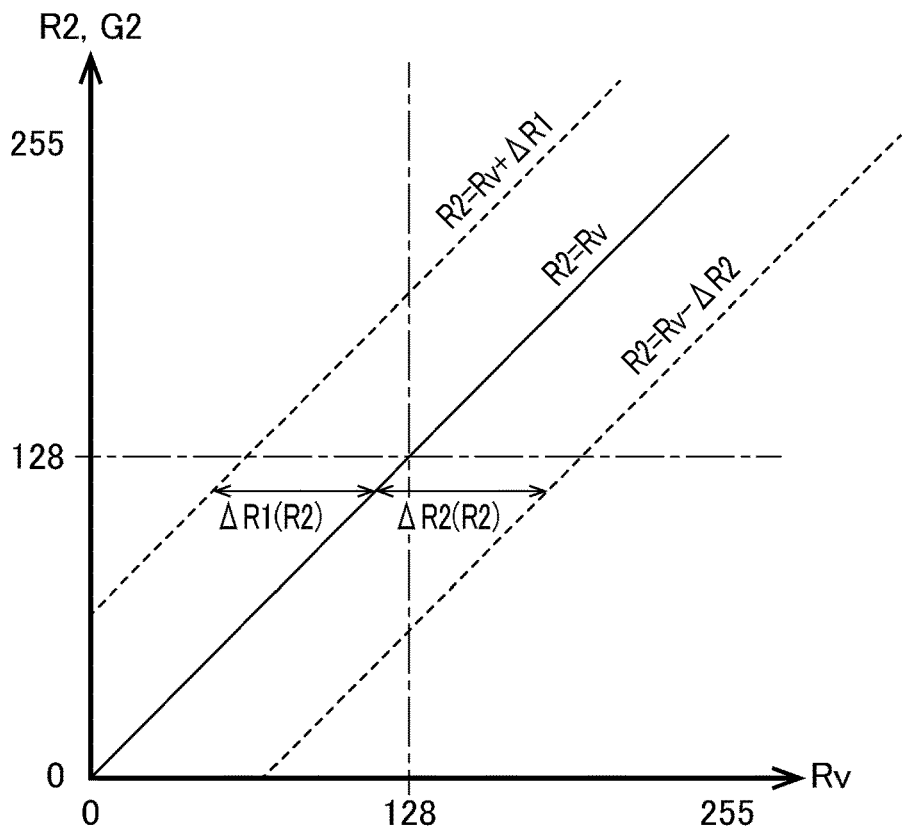

FIG. 7 indicates a changeable range of a red color component of the test image according to the first embodiment of the present disclosure.

Figure 8:
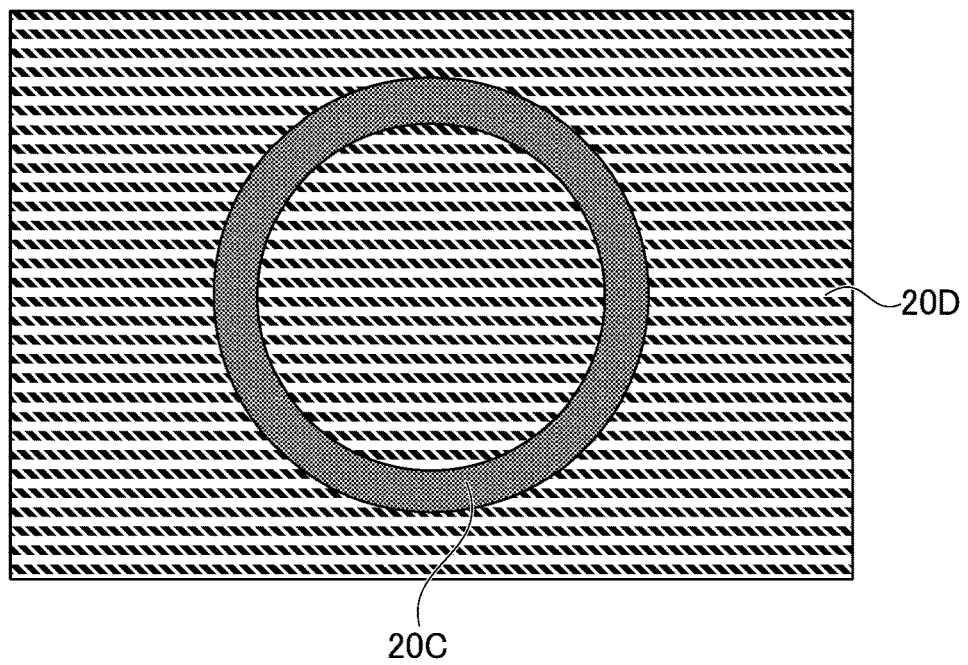

FIG. 8 is a test image according to the first embodiment of the present disclosure.

Figure 9:
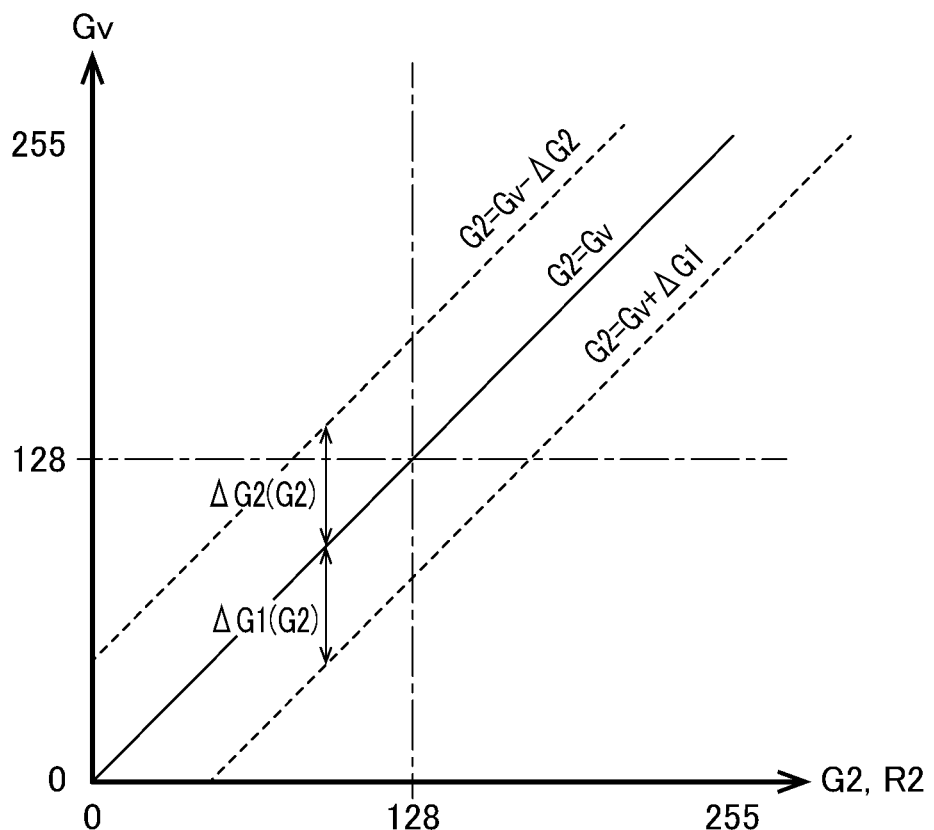

FIG. 9 indicates a changeable range of a green color component of the test image according to the first embodiment of the present disclosure.

Figure 10:
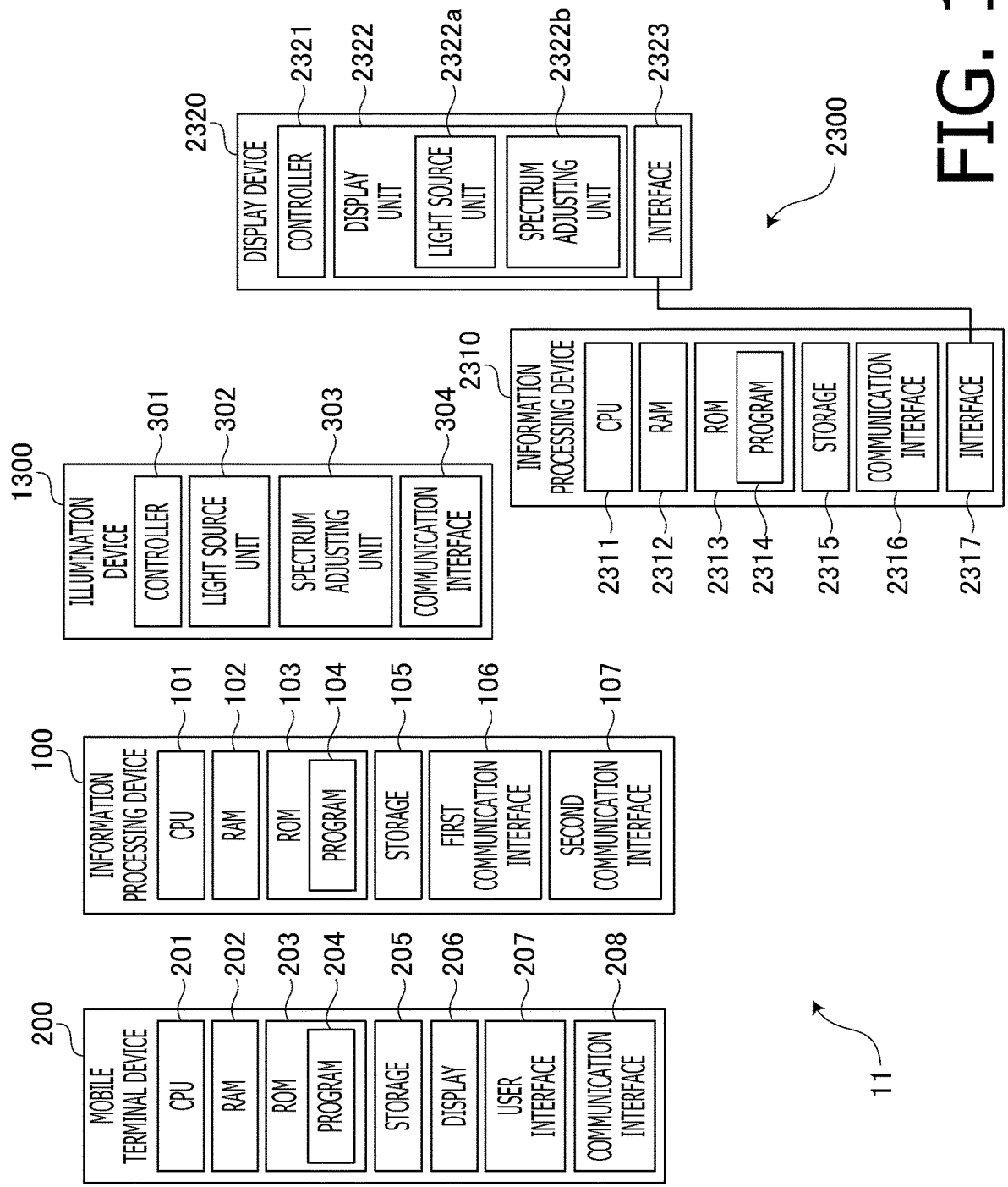

FIG. 10 is a schematic diagram of a modified illumination light adjusting system according to the first embodiment of the present disclosure of the present disclosure.

Figure 11:
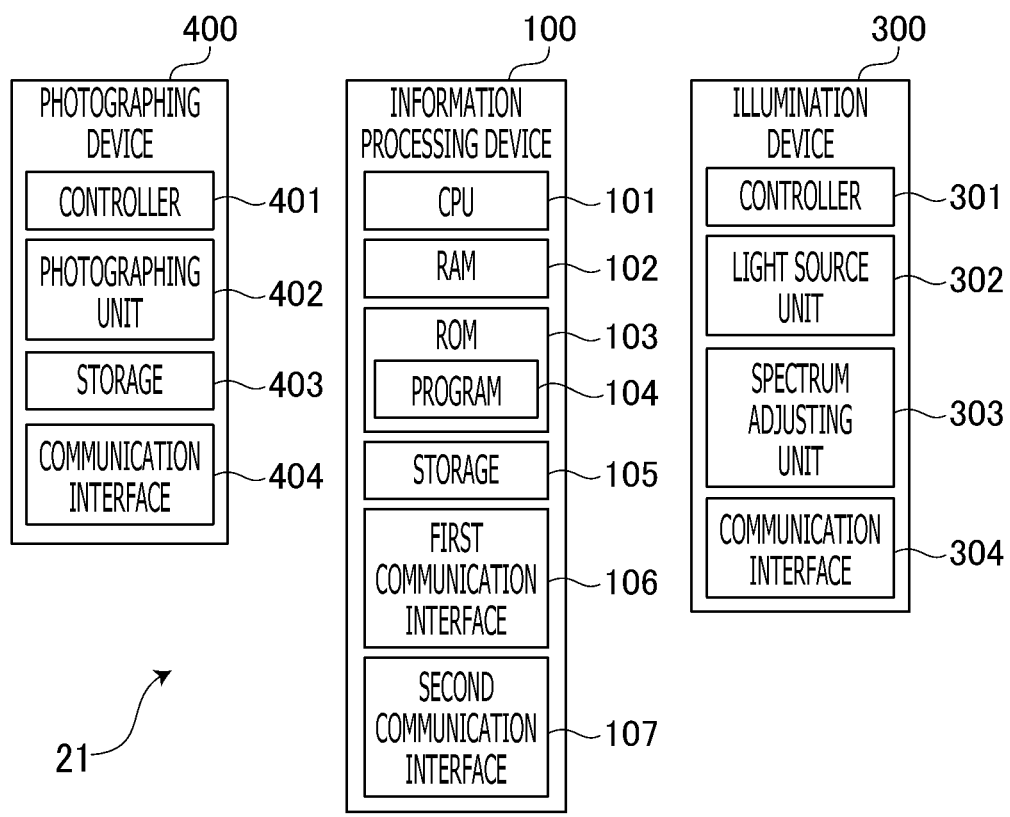

FIG. 11 is a schematic diagram of an illumination light adjusting system according to a second embodiment of the present disclosure of the present disclosure.

Figure 12:
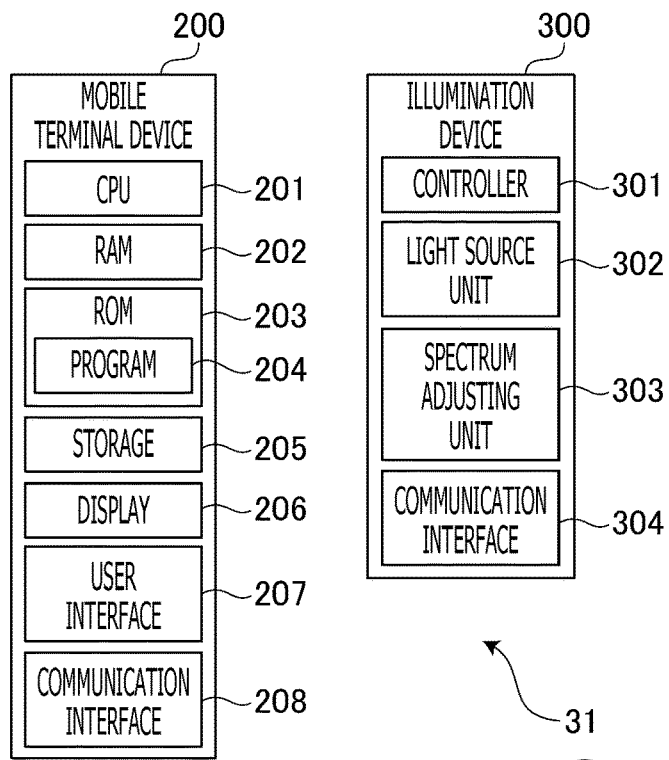

FIG. 12 is a schematic diagram of an illumination light adjusting system according to a third embodiment of the present disclosure of the present disclosure.

Figure 13:
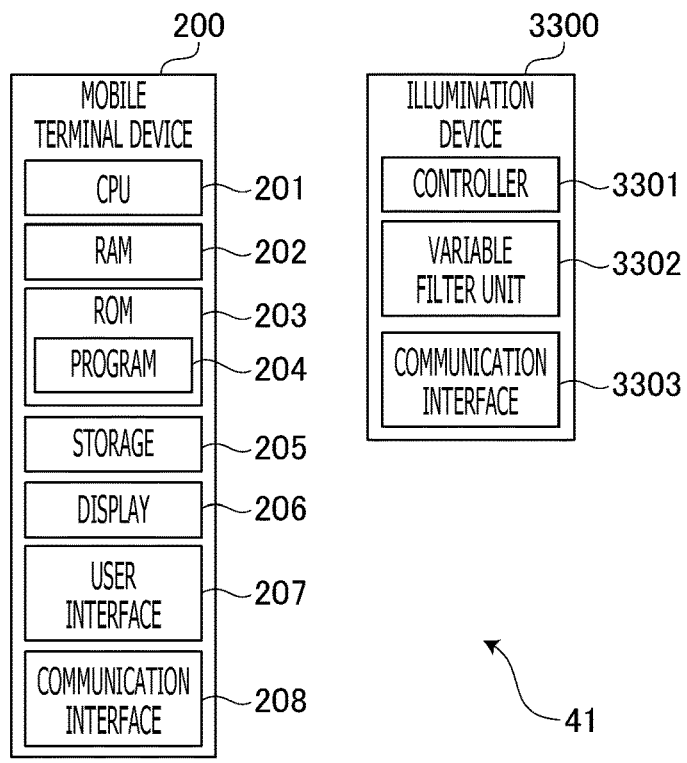

FIG. 13 is a schematic diagram of an illumination light adjusting system according to a fourth embodiment of the present disclosure of the present disclosure.

Figure 14A:
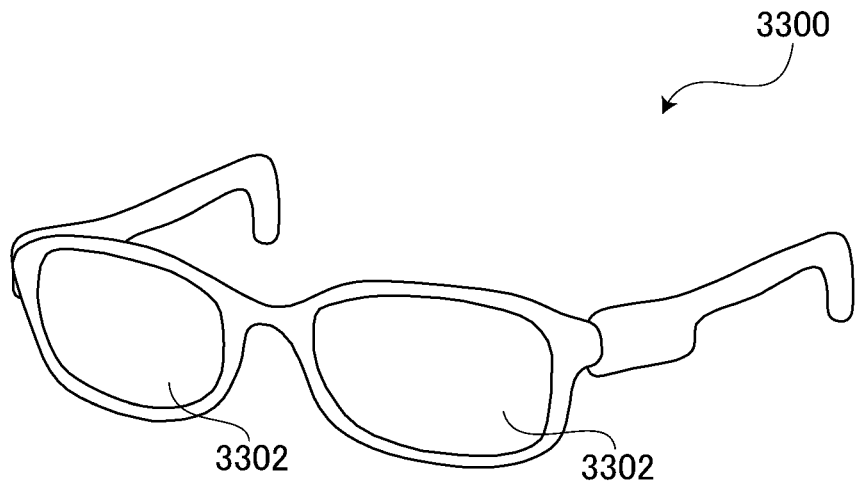

FIG. 14A is a perspective view of an illumination device according to the fourth embodiment of the present disclosure.

Figure 14B:
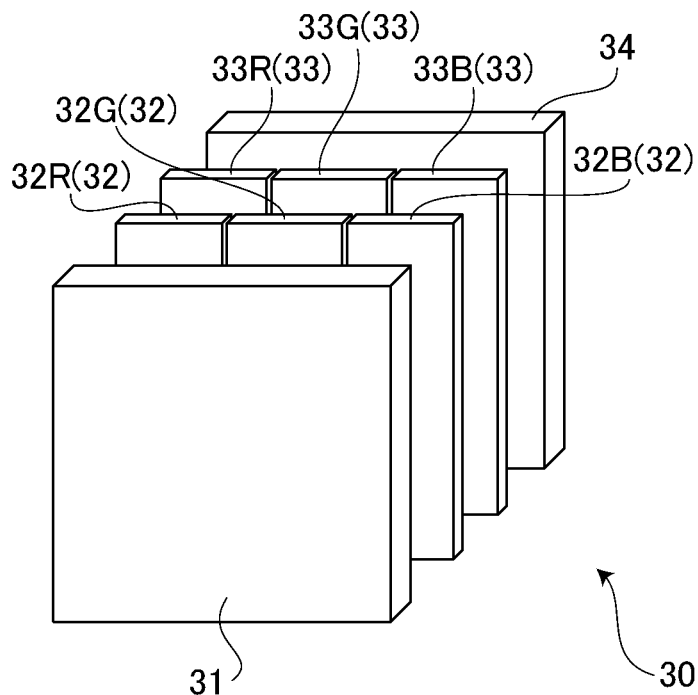

FIG. 14B is a schematic diagram of a variable filter unit according to the fourth embodiment of the present disclosure.

DESCRIPTION OF THE ILLUSTRATIVE EMBODIMENT

Hereinafter, an illustrative embodiment according to aspects of the present disclosure will be described referring to the accompanying drawings.

First Embodiment

Figure 1:
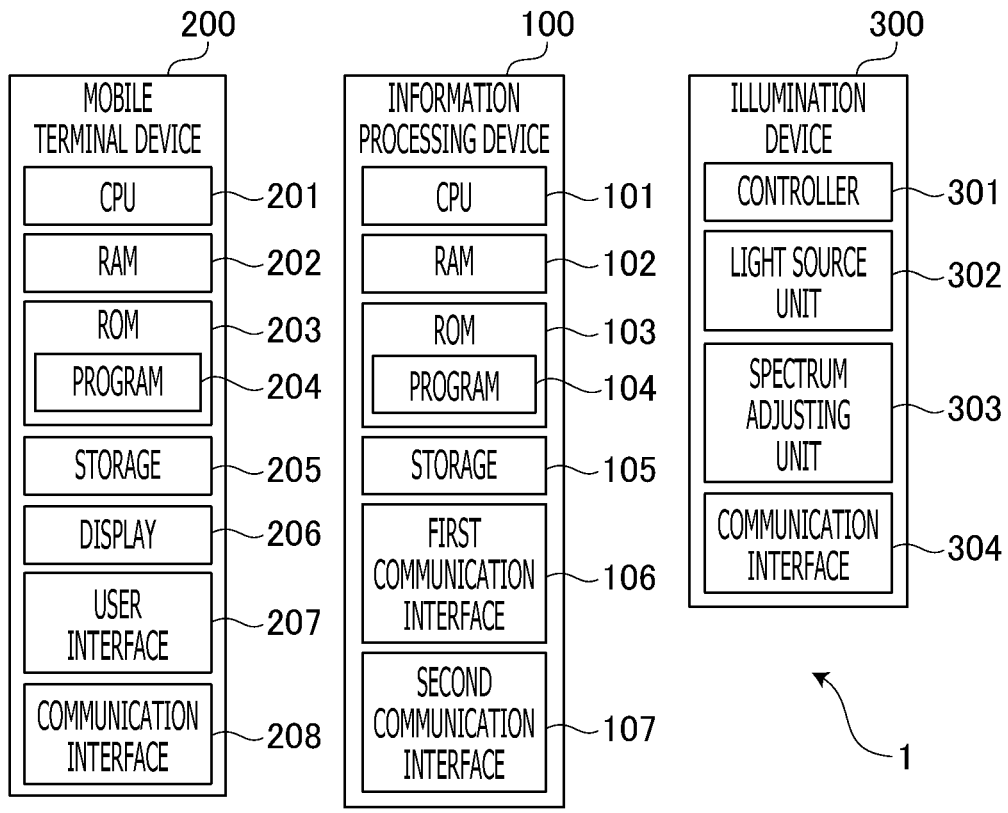
FIG. 1 is a schematic diagram of an illumination light adjusting system according to a first embodiment of the present disclosure.

FIG. 1 shows a schematic diagram of an illumination light adjusting system 1 according to a first embodiment of the present disclosure. The illumination light adjusting system 1 includes an information processing device 100, a mobile terminal device 200, and an illumination device 300.

The information processing device 100 may be, for example, a multipurpose information processing device such as a PC or a server, or a dedicated device for the illumination light adjusting system 1. The information processing device 100 includes a CPU (Central Processing Unit) 101, a RAM (Random Access Memory) 102, a ROM (Read Only Memory) 103, a program 104, a storage 105, a first communication interface 106, and a second communication interface 107. The CPU 101 executes the program 104 stored in the ROM 103. The RAM 102 is used as a temporal storage area when the CPU 101 executes the program 104. The program 104 includes an application and an OS (Operating System) or the like used to control the information processing device 100. The storage 105 stores various types of data such as spectrum information which will be explained later. The storage 105 is, for example, an HDD (Hard Disk Drive), an SSD (Solid State Drive), or a portable recording medium configured to attached to or detached from the information processing device 100. The first communication interface 106 is used for wired or wireless communication with the mobile terminal device 200. The second communication interface 107 is used for wired or wireless communication with the illumination device 300. It is noted that the information processing device 100 may communicate with both the mobile terminal device 200 and the illumination device 300 using a single communication interface.

The mobile terminal device 200 is, for example, a portable terminal device such as a smartphone, a tablet terminal, or a note PC. The mobile terminal device 200 includes a CPU 201, a RAM 202, a ROM 203, a program 204, a storage 205, a display 206, a user interface 207, and a communication interface 208. The CPU 201 executes the program 204 stored in the ROM 203. The RAM 202 is used as a temporal storage area when the CPU 201 executes the program 204.

The program 204 includes an application and an OS or the like used to control the mobile terminal device 200. The storage 205 stores various types of data such as the color vision information which will be explained later. The storage 205 is, for example, an HDD, an SSD, or a portable recording medium configured to be attached to or detached from the mobile terminal device 200. The display 206 is configured to display various types of information in accordance with the executed program 204. The user interface 207 is configured to receive an input operation of the user. The communication interface 208 is used for wired or wireless communication with the information processing device 100.

The storage 205 of the mobile terminal device 200 stores color vision information indicating the color vision characteristics of the user using the mobile terminal device 200. The color vision characteristics are ones measured by the mobile terminal device 200 or other measuring devices. The color vision information is information indicating a type of the color vision deficiency (e.g., the color blindness, the color weakness, of the Irlen syndrome) and degree thereof. For example, the color vision information is information indicating a visual sensitivity for light in a particular color or information indicating ate least one of a ratio and difference between visual sensitivities to light of a plurality of different colors. It is noted that the color vision information stored in the storage 205 need not include all the above pieces of information, and may include at least one of them.

The illumination device 300 is, for example, an illumination device, a display device (e.g., a liquid crystal display or a CRT (Cathode Ray Tube) display), or a projector. The illumination device 300 includes a controller 301, a light source unit 302, a spectrum adjusting unit 303 and a communication interface 304. The light source unit 302 includes a light emitting device such as an LED, an LED, an organic EL, an incandescent lamp, or a chrysanthemum lamp. When the illumination device 300 is the liquid crystal display, the light source unit 302 includes, for example, a light source and a light guide plate that guides the illumination light emitted from the light source, or a diffuser plate that diffuses the illumination light. The spectrum adjusting unit 303 is configured to change a spectrum (i.e., the wavelength characteristics) of the illumination light emitted from the light source unit 302. For example, the spectrum adjusting unit 303 may be a circuit configured to control the light source unit 302. Further, the spectrum adjusting unit 303 may be included in the controller 301, and the controller 301 may control the light source unit 302. The communication interface 304 is used for wired or wireless communication with the information processing device 100. The controller 301 is configured to change an intensity or spectrum of the illumination light by controlling operations of the light source unit 302 and the spectrum adjusting unit 303.

The spectrum adjusting unit 303 of the illumination device 300 is configured to change a wavelength band through which the illumination light is transmitted or reflected. The spectrum adjusting unit 303 includes, for example, a transmission type or reflection type of a spatial light modulator and a color filter through which a light of a specific wavelength band can be transmitted. The spatial light modulator is, for example, a liquid panel of a DMD (Digital Mirror Device). The spectrum adjusting unit 303 may be a plurality of types of color filters which change the spectrum of the illumination light by being inserted into or removed from a light path.

The light source unit 302 may serve as a function of the spectrum adjusting unit 303. When the light source unit 302 includes a plurality of light sources of which emission wavelengths are different from each other, the spectrum of the illumination light can be changed by controlling light intensity of each light source.

Figure 2:
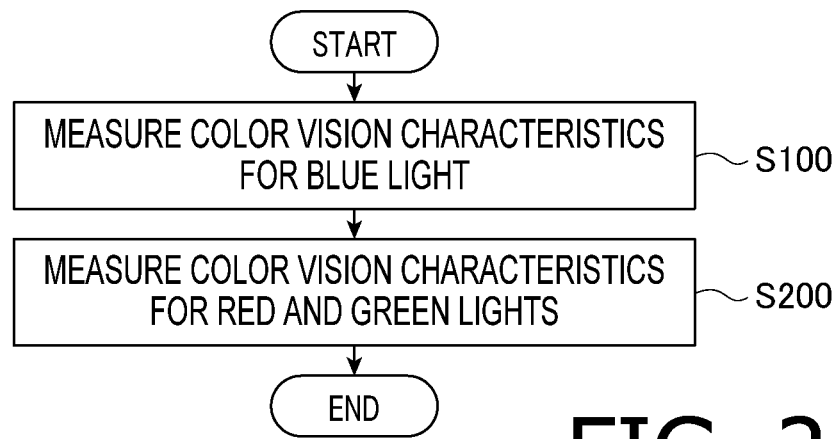
FIG. 2 is a flowchart of a measuring method of the color vision characteristics according to the first embodiment of the present disclosure.

Hereinafter, a measuring method of the color vision characteristics of the user will be explained. The color vision characteristics may be measured by the mobile terminal device 200. FIG. 2 shows a flowchart of the measuring method of the color vision characteristics. A color adjusting method indicated in FIG. 2 is started as the CPU 201 executed the program 204.

In step S100, the color vision characteristics of the user for a blue light is mainly measured. In step S200, the color vision characteristics of the user for a red light and a green light are measured. In the following, steps S100 and S200 will be explained in detail.

Step S100

Figure 3:
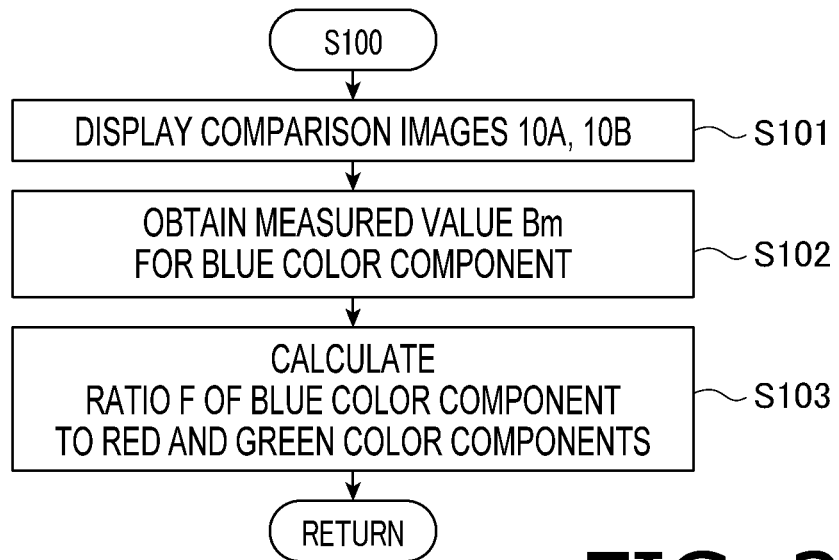
FIG. 3 is a flowchart of a testing method of the color vision characteristics of a user for blue light according to the first embodiment of the present disclosure.

FIG. 3 shows a flow chart of step S100 in detail. The color vision characteristics have individual difference, and light sensitivity varies due to a wavelength band. The case of a high light sensitivity for a light of a specific wavelength (especially, the blue light) is called photo-allergy or the Irlen syndrome. Irlen syndrome is thought to be due to the unusual high sensitivity of S-cone cells for the blue light. In S100, the color vision characteristics of the user for the blue light and the ratio (or the difference) between the color vision characteristics for the blue light and lights of colors other than blue.

Step S101 of FIG. 3

Figure 4:
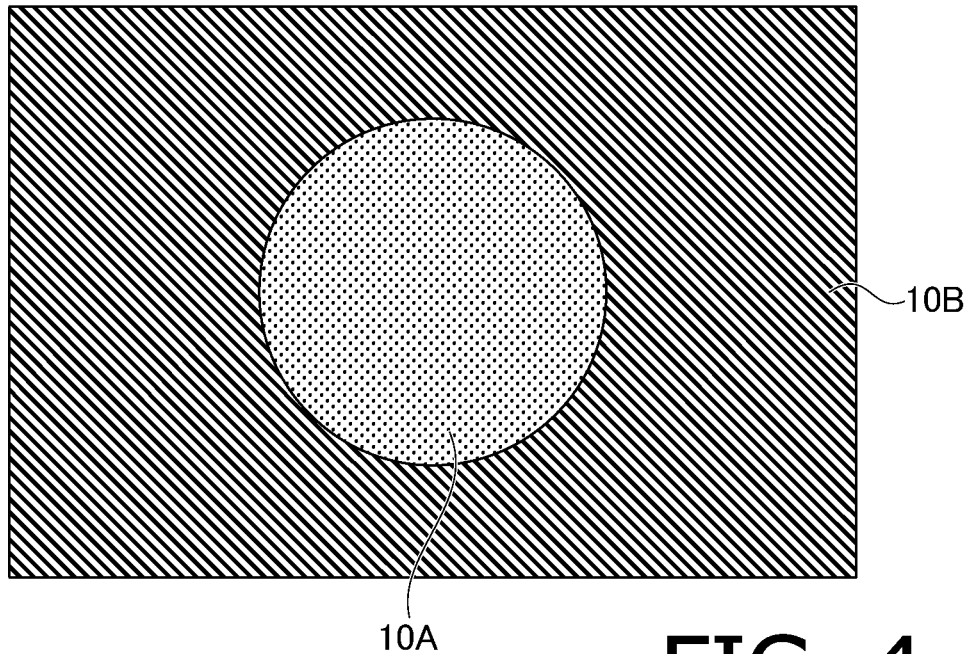
FIG. 4 is a comparison image according to the first embodiment of the present disclosure.

In step S101, two comparison images 10A, 10B are displayed on the display 206. Respective images 10A, 10B have different colors. FIG. 4 shows an example of the comparison images 10A, 10B displayed on the display 206. In this example, a circular comparison image 10A is displayed in the rectangular comparison image 10B. It is noted that sizes or shapes of the comparison images 10A, 10B are no limited to the example shown in FIG. 4 as long as the two comparison images 10A, 10B are arranged closely such that the user can recognize the two comparison images 10A, 10B at the same time. For example, the comparison image 10A may be a rectangular figure or a character such as a number or an alphabet. Alternatively, the respective comparison images 10A, 10B may have rectangular shapes and be displayed side by side.

When colors of the comparison images 10A, 10B are represented by color components (R, G, B) in an RGB color space, the color components of the comparison image 10A are (R1, 0,B1), and the color components are (0, G1, B1). That is, between the comparison images 10A and 10B, magnitudes (i.e., spectrum intensities) of the blue color components are equal. Further, it is preferable that the red color component R1 and the green color component G1 have the same magnitude.

A magnitude of each color component of the comparison images 10A and 10B is individually variable. For example, when the color components in each comparison image are represented by an R image signal, a G image signal and a B image signal of 8-bit (i.e., 256 tones), the magnitude of each color component of the comparison images is variable between 0 and 255.

Step S102 of FIG. 3

In step S102, an optimum magnitude of the blue color component for the user is examined using the comparison images 10A and 10B displayed in step S101. Concretely, in a state where the user is looking at the comparison images 10A and 10B displayed on the display 206, the magnitude of the blue color component B1 of the comparison image 10A and the magnitude of the blue color component B1 of the comparison image 10B are changed at the same time the two blue color components B1 of the comparison images 10A and 10B are equal to each other. At the time, the red color component R1 of the comparison image 10A and the green color component G1 of the comparison image 10B are fixed to, for example, a central value in a variable range (e.g., around 128 in 8-bit). Then, a blue color component B1, which is a value that causes the user to visually recognize a color difference between the comparison image 10A and the comparison image 10B most clearly, is determined. The determined blue color component B1 is stored in the storage 205 as a measured valued Bm.

According to characteristics of the color sensitivity of the user or a determination criterion of the user for clarity, a plurality of conditions (i.e., the measured value Bm of the blue color component) for achieving the highest visibility for the user to visually recognize the color difference between the comparison image 10A and the comparison image 10B can exist. In such a case, an averaged value or a central value of a plurality of blue color components B1 such that the user recognizes the color difference most clearly, may be set as the measured value Bm. Or, one of the plurality of blue color components B1 such that the user recognizes the color difference most clearly may be selected as the measured value Bm based on preference of the user (e.g., preference for colors or easiness to see).

If the user has the Irlen syndrome, when the blue color components B1 of the comparison images 10A and 10B are high, the user might feel dazzled by the comparison images 10A and 10B, and it is difficult for the user to recognize the color difference between the comparison images 10A and 10B. In that case, the measured value Bm may be smaller than a maximum value Bmax (e.g., 255 in 8-bit) within a settable range of the blue color component.

In contrast, if the user does not have the Irlen syndrome, even when the blue color components B1 of the comparison images 10A and 10B are high, the user may not feel dazzled by the comparison images 10A and 10B. Furthermore, as the blue color component B1 becomes higher, the user may feel that each comparison image 10A and 10B is bright, and it may be easier for the user to recognize the color difference between the comparison images 10A and 10B. Thus, the measured value Bm for the user who does not have the Irlen syndrome is higher than the measured value Bm for the user who has the Irlen syndrome.

Step S103 of FIG. 3

In step S103, an optimum ratio F of the blue color component to the red and green color components for the user is examined using the comparison images 10A and 10B. Concretely, in a state where the user is looking at the comparison images 10A and 10B displayed on the display 206, the magnitude of the red color component R1 of the comparison image 10A and the magnitude of the green color component G1 of the comparison image 10B are changed in such a manner that the red color component R1 and the green color component G1 are equal to each other. At the time, the blue color components B1 of the comparison images 10A and 10B are fixed to the measured value Bm. It is noted that the red color component R1 in of comparison image 10A and the green color component G1 of the comparison image 10B do not have to be exactly the same value.

In step S103, the magnitude of the red color component Rc of the comparison image 10A and the magnitude of the green color component Gc of the comparison image 10B, at the time when the user recognizes the color difference between t the comparison images 10A and 10B most clearly, are measured. After the red color component Rc and the green color component Gc are measured, a measurement value Id and the ratio F are calculated in accordance with the following formula 1 and stored in the storage 205.

$$Id=(Rc+Gc)/2$$

$$F=Id/Bm \qquad \text{(Formula 1)}$$

where the measurement value Id is an average of the red color component Rc and the green color component Gc. It is noted that, since the red color component Rc and the green color component Gc are maintained to have the same value in step S103, one of Rc and Gc may be set as the measurement value Id. The ratio F is a ratio of the measured value Bm of the blue color component to the red and green color component Rc and Gc.

If the user has the Irlen syndrome, generally, the sensitivity of the user for red light of green light is lower than that for blue light. In that case, the measurement value Id becomes higher that the measured value Bm, and the ratio F becomes higher than one.

Step S200

Figure 5:
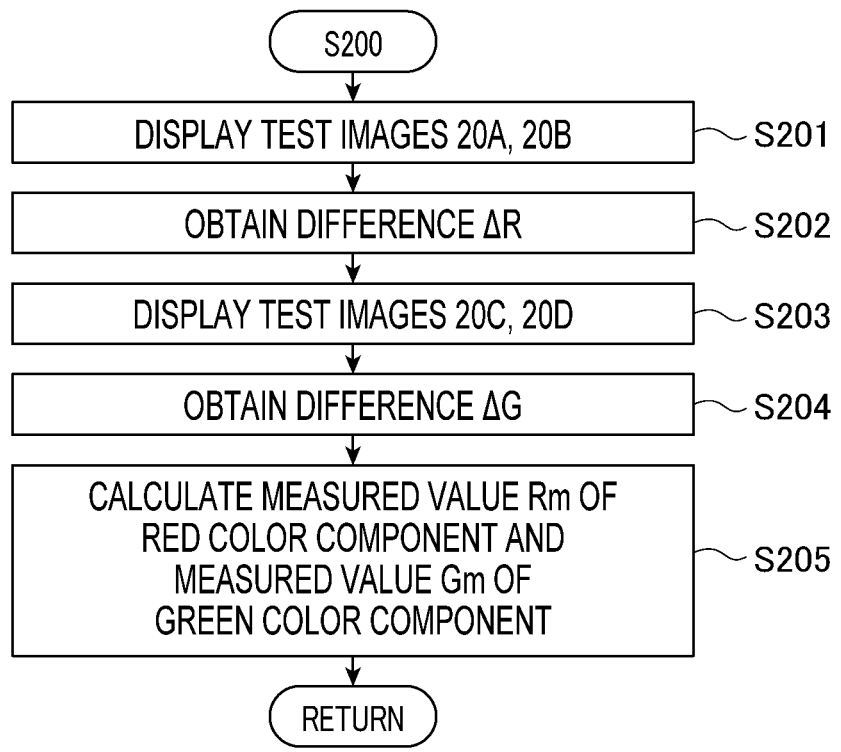
FIG. 5 is a flowchart of a testing method of the color vision characteristics of a user for red and green lights according to the first embodiment of the present disclosure.

Next, a detail of step S200 will be described. FIG. 5 shows a flowchart illustrating a detail of step S200. In step S200, color sensitivities of the user for red light and green light are measured.

Step S201 of FIG. 5

Figure 6:
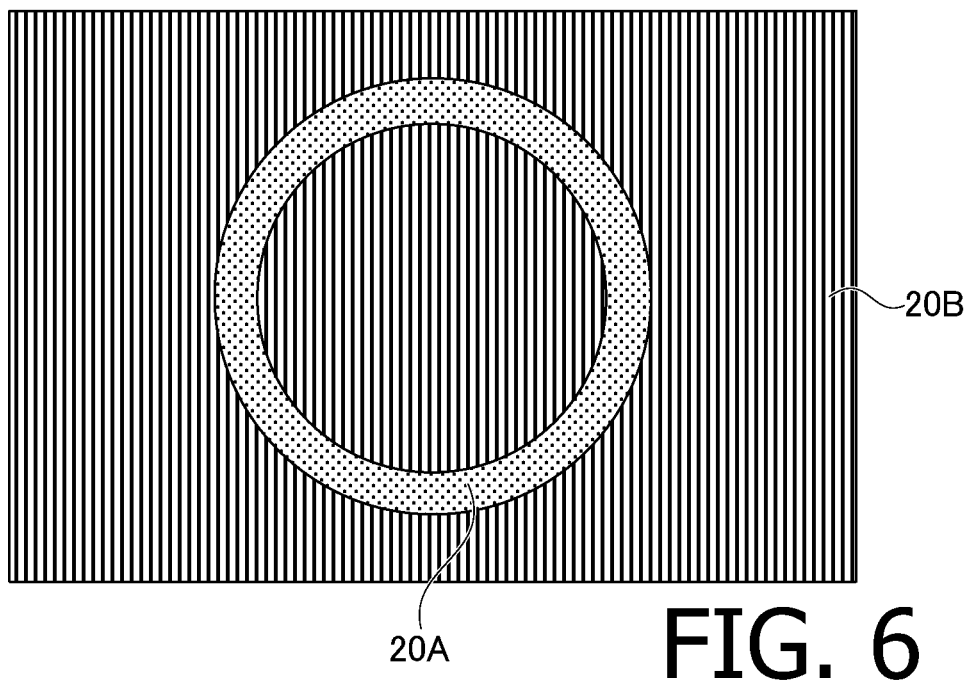
FIG. 6 is a test image according to the first embodiment of the present disclosure.

In step S201, two test images 20A and 20B are displayed on the display 206. FIG. 6 shows an example of the test images 20A and 20B displayed on the display 206. In the example, the test image 20A having a ring shape is displayed within the test image 20B having a rectangular shape. It is noted that the test images 20A and 20B may be arranged closely such that the user can visibly recognize the two test images at the same time. Further, sizes or shapes of the test images 20A and 20B are not limited to the example shown in FIG. 6. Specifically, the test image 20A may have rectangular shapes or represent a character such as a number or an alphabet. Both the test images 20A and 20B may have rectangular shapes and be displayed side by side.

The color components of the test image 20A are (Rv, G2, B2), and the color components of the test image 20B are (R2, G2, B2). That is, the test image 20A and the test image 20B have the same green and blue color components. Further, a magnitude of the red color component R2 and a magnitude of the green color components G2 are equal. The red color component R2 and the green color components G2 may be a central value in a settable range (e.g., around 128 in 8-bit) or the measured values Rc and Gc measured in step S103, respectively. Further, the blue color component B2 is the measured value Bm measure in step S102, or zero. It is noted that each of the color components R2, G2 and B2 is not limited to the above value, and may be changed from the above value such that the test images 20A and 20B become easy to see for the user.

Step S202 of FIG. 5

In step S202, a color sensitivity of the user for red light is examined using the test images 20A and 20B display in step S201. Concretely, in a state where the user is looking at the test images 20A and 20B displayed on the display 206, a magnitude of the red color component Rv of the test image 20A is changed. An initial value of the red color component of the test image 20A is set to R2. Therefore, before the magnitude of the red color component Rv is changed, the test image 20A and the test image 20B have the same color. Then, a red color component Rs1, which is a value that color differences between the test image 20A and the test image 20B is recognizable to the user, is measured. Further, a difference ΔR is calculated based on the Rs1 and R2 in accordance with the following formula 2 and stored in the storage 205.

$$\Delta R \times |R2-Rs1| \qquad \text{(Formula 2)}$$

It is noted that, in step S202, the red color component Rv may be changed to a value higher than the initial value R2 or a value lower than the initial value R2. The difference ΔR may be measured in both cases where the red color component is changed to be higher than the initial value and where the red color component is changed to be lower than the initial value. In this case, an average value of two differences ΔR may stored as the difference ΔR.

Further, in step S202, not only the red color component Rv, the red color component R2 and the green color component G2 may be changed in such a manner that the magnitude of the red color component R2 and the magnitude of the green color component G2 are equal to each other. In this case, the red color component Rs1, which is the magnitude of the red color component Rv that the color difference between the test image 20A and the test image 20B is recognizable for the user, is measured in each red color component R2 (each green color component G2). Further, the difference ΔR is calculated in each red color component Rs1. A representative value (e.g., an average value, a central value or a most frequent value) of the plurality of the differences ΔR may be stored as the difference ΔR.

FIG. 7 shows an area in which the red color component Rv of the test image 20A and the red color component R2 of the test image 20B can be varied. In FIG. 7, the horizontal axis indicates the red color component Rv of the test image 20A, and the vertical axis indicates the red color component R2 of the test image 20B. Since the red color component R2 of the test image 20A and the green color component G2 of the test image 20B are maintained to have the same value, the vertical axis of FIG. 7 also indicates the green color component G2. In FIG. 7, each color component is represented in 8-bit (i.e., 256 tones).

In FIG. 7, on the straight line of R2=Rv, the test image 20A and the test image 20B have the same color components (R2, G2, B2). Therefore, when R2=Rv, the color difference between the test image 20A and the test image 20B is unrecognizable for the user regardless of the color vision characteristics thereof.

In step S202, when the red color component Rv of the test image 20A is changed, a coordinate in FIG. 7 is moved in the right and left direction (i.e., along the horizontal axis) from the straight line of R2=Rv. At the time, although the red color component of the test image 20A is changed, none of the color components of the test image 20B is changed. When the color difference between the test image 20A and the test image 20B becomes recognizable for the user, a change amount of the red color component Rv is the difference ΔR. As shown in FIG. 7, the difference ΔR is measured in both sides of the straight line R2=Rv in the right and left direction with respect to each red color component R2 (green color component G2) as the differences ΔR1 and ΔR2, respectively. One of the differences ΔR1 and ΔR2 may be stored as the difference ΔR. Alternatively, an average of the two differences ΔR1 and ΔR2 may be stored as the difference ΔR.

Further, in step S202, the red color component R2 (and the green color component G2) may be also changed. In that case, the difference ΔR(R2) is measured in each red color component R2. Where the difference ΔR(R2) is, for example, an average of the difference ΔR1(R2) and ΔR2(R2) represented in right and left sides of the straight line of R2=Rv. In this case, a representative value of the plurality of differences ΔR(R2) is stored as the difference ΔR.

It is noted that, in step S202, the red color component Rv and the red color component R2 (and the green color component G2) are not necessary to be changed by one tone. For example, it may be changed by five tones or ten tones. The red color component R2 is not necessary to be changed in a full range of a variable range (e.g., from 0 to 255 in 8-bit). For example, since the brightness of each of the test image 20A and the test image 20B becomes lower as the red color component R2 is changed smaller, there is a possibility that the difference ΔR cannot be measured correctly. Therefore, the red color component R2 may be changed within a range equal to or higher than the initial value (e.g., 128 in 8-bit or Rc). Further, in step S202, the red color component R2 may not be changed and fixed to the initial value.

Step S203 of FIG. 5

In step S203, two test images 20C and 20D are displayed on the display 206. FIG. 8 shows an example of the test images 20C and 20D displayed on the display 206. In the examples, the test image 20C having a circular shape is displayed within the test image 20D having a rectangular shape. It is noted that the test images 20C and 20D may be displayed in proximity to each other such that the user can visibly recognize the test images the same time. Further, sizes or shapes of the test images 20C and 20D are not limited to the examples shown in FIG. 8. Specifically, the test image 20C may have a rectangular shape and may represent a character such as a number or an alphabet. Both the test images 20C and 20D may have rectangular shapes and be displayed side by side.

The color components of the test image 20C are (R2, Gv, B2), and the color components of the test image 20D are (R2, G2, B2). That is, the test image 20C and the test image 20D have the same red and blue color components. Further, a magnitude of the red color component R2 and a magnitude of the green color components G2 are equal to each other. For example, The red color component R2 and the green color components G2 is a central value in a settable range (e.g., around 128 in 8-bit). Alternatively, the red color component R2 and the green color components G2 may be the measured value Rc and Gc measured in step S103, respectively. Further, the blue color component B2 is the measured value Bm measure in step S102, or zero. It is noted that each of the color components R2, G2 and B2 is not limited to the above value, and may be changed from the above value such that the test images 20C and 20D become easy to see for the user.

Step S204 of FIG. 5

In step S204, a color sensitivity of the user for green light is examined using the test images 20C and 20D display in step S203. Concretely, in a state where the user is looking at the test images 20C and 20D displayed on the display 206, the magnitude of the green color component Gv of the test image 20C is changed. An initial value of the green color component of the test image 20C is set to G2. Therefore, before the user changes the magnitude of the green color component Gv, the test image 20C and the test image 20D have the same color. Then, a green color component Gs1, which is a value that color differences between the test image 20C and the test image 20D is recognizable for the user, is measured. Further, based on Gs1 and G2, a difference ΔG is calculated in accordance with the following formula 3 and stored in the storage 205.

$$\Delta G = |G2 - Gs1| \quad \text{(Formula 3)}$$

It is noted that, in step S204, the green color component Gv may be changed to a value higher than the initial value G2 or a value lower than the initial value G2. The difference ΔG may be measured in both cases where the green color component is changed to be higher than the initial value and where the green color component is changed to be lower than the initial value. In this case, the average value of two differences ΔG is stored as the difference ΔG.

Further, in step S204, not only the green color component Gv, the red color component R2, and the green color component G2 may be changed in such a manner that the red color component R2 and the green color component G2 are equal to each other. In this case, the green color component Gs1, which is a magnitude of the green color component Gv that the color difference between the test image 20C and the test image 20D is recognizable for the user, is measured in each green color component G2 (each red color component R2). Further, the difference ΔG is calculated in each green color component Gs1. A representative value (e.g., an average value, a central value, or a most frequent value) of the plurality of the differences ΔG is stored as the difference ΔG.

FIG. 9 shows an area in which the green color component Gv of the test image 20C and the green color component G2 of the test image 20D can be varied. In FIG. 9, the horizontal axis indicates the green color component Gv of the test image 20C, and the vertical axis indicates the green color component G2 of the test image 20D. Since the green color component G2 of the test image 20C and the red color components R2 of the test image 20C and the test image 20D are maintained to have the same value, the vertical axis of FIG. 9 also indicates the red color component R2. In FIG. 9, each color component is represented in 8-bit (i.e., 256 tones).

In FIG. 9, on the straight line of G2=Gv, the test image 20C and the test image 20D have the same color components (R2, G2, B2). Therefore, when G2=Gv, the user cannot recognize the color difference between the test image 20C and the test image 20D regardless of his/her color vision characteristics.

In step S204, when the green color component Gv of the test image 20C is changed, a coordinate in FIG. 9 is moved in the up and down direction (i.e., along the vertical axis) from the straight line of G2=Gv. At the time, although the green color component of the test image 20C is changed, none of the color components of the test image 20D is changed. When the color difference between the test image 20C and the test image 20D becomes recognizable for the user, a change amount of the green color component Gv is the difference ΔG. As shown in FIG. 9, the difference ΔG is measured in both sides of the straight line G2=Gv in the up and down direction with respect to each green color component G2 (each red color component R2) as the differences ΔG1 and ΔG2, respectively. One of the differences between ΔG1 and ΔG2 may be stored as the difference ΔG. Otherwise, an average of the two differences ΔG1 and ΔG2 may be stored as the difference ΔG.

Further, in step S204, the green color component G2 (and the red color component R2) may be also changed. In that case, the difference ΔG(G2) is measured in each green color component G2. Where the difference ΔG(G2) is, for example, an average of the difference ΔG1(G2) and ΔG2(G2) represented in up and down sides of the straight line of G2=Gv. In this case, a representative value of the plurality of differences ΔG(G2) is stored as the difference ΔG.

It is noted that, in step S204, the green color component Gv and the green color component G2 (the red color component R2) are not necessary to be changed by one tone.

For example, it may be changed by five tones or ten tones. The green color component G2 is not necessary to be changed in a full range of a variable range (e.g., from 0 to 255 in 8-bit). For example, the green color component G2 may be changed within a range equal to or higher than the initial value (e.g., 128 in 8-bit or Gc). Further, in step S204, the green color component G2 may not be changed and fixed to the initial value.

[Step S205 of FIG. 5]

In step S205, measurement values Rm and Gm are calculated based on the difference ΔR and the difference ΔG. Concretely, the measurement values Rm and Gm are calculated in accordance with the following formula 4.

$$Rm = \Delta R / \max(\Delta R, \Delta G)$$

$$Gm = \Delta G / \max(\Delta R, \Delta G) \quad \text{(Formula 4)}$$

where "max (ΔR, ΔG)" means a bigger one of ΔR and ΔG. The calculated measurement values Rm and Gm are stored in the predetermined memory space.

The differences ΔR and ΔG, which are measured in step S202 and S204, correspond to the visual sensitivities of the user to the red light and the green light, respectively. For example, in step S202, only the red color component of the test image 20A is changed from a state where the test images 20A and 20B have the same color (e.g., from a state where the color components of the test image 20A are (R2, G2, B2)). When the visual sensitivity of the user to the red light is relatively high, the user can visually recognize the difference between the test images 20A and 20B can without significantly changing the red component of the test image 20A. On the other hand, when the user's sensitivity to the red light is relatively low, it is difficult for the user to recognize the change in the red component of the test image 20A. Therefore, it is necessary to significantly change the red component of the test image 20A until the user can recognize the difference between the test image 20A and the test image 20B. Thus, the difference ΔR (and the measured value Rm) is smaller the higher the user's sensitivity to the red light and larger the lower the user's sensitivity to the red light.

Similar to the difference ΔR (and the measured value Rm), the difference ΔG (and the measured value Gm) is smaller the higher the user's sensitivity to the green light and larger the lower the user's sensitivity to the green light. Thus, the ratio of the difference ΔR to the difference ΔG (and the ratio of the measured value ΔR to the measured value ΔG) corresponds to the ratio of the sensitivity of the user for the red light to the sensitivity of the user for the green light.

By the above measurement method, the color vision characteristics (i.e., the measured value Rm, the measured value Gm, and the ratio F) corresponding to the visual sensitivity of the user to the red, green, and blue light are measured, and recorded in the storage 205 of the mobile terminal device 200 as the color vision information. The above-mentioned measurement method of the color vision characteristics of the user is one of examples of the measurement method. The color vision characteristics of the user may be measured by another device or another method and recorded in the mobile terminal device 200. Further, the color vision characteristics of the user recorded in the mobile terminal device 200 are not limited to the measured value Rm, the measured value Gm, and the ratio F. Any one or more of these color vision characteristics may be recorded. Alternatively, the color vision information recorded in the mobile terminal device 200 may be any information other than the measured value Rm, the measured value Gm, and the ratio F, as long as it indicates the color vision characteristics of the user.

Next, an example of the illumination light adjusting method by the illumination light adjusting system 1 of the present embodiment will be described. In the following, as an example, a case where the user having a mobile terminal device 200 enters a room where the information processing device 100 and the illumination device 300 are installed will be described.

When the user having the mobile terminal device 200 enters the room where the information processing device 100 and the illumination device 300 are installed, communication is established between the mobile terminal device 200 and the information processing device 100. The communication between the mobile terminal device 200 and the information processing device 100 is, for example, communication by wireless LAN or communication by Bluetooth™. When the communication is established between the mobile terminal device 200 and the information processing device 100, the mobile terminal device 200 reads out the color vision information (for example, the measured value Rm, the measured value Gm, the ratio F) indicating the color vision characteristics of the user. The read color vision information is transmitted to the information processing device 100 via the communication interface 208.

The storage 105 of the information processing apparatus 100 stores the spectrum information used to adjust the spectrum of the illumination light. The spectrum information indicates the spectrum of the illumination light suitable for the color vision characteristics of the user. The spectrum information is, for example, the intensity of the illumination light in each of the red, green, and blue wavelength bands, or the ratio or difference of the light intensity between the respective wavelength bands. The spectrum information may be, for example, a table including various color vision characteristics and spectrum information corresponding to each color vision characteristics. Alternatively, the information processing device 100 may have a calculation program used to calculate the spectrum information based on the color vision information received from the mobile terminal device 200.

The information processing device 100 identifies the spectrum information suitable for the color vision characteristics of the user based on the color vision information received from the mobile terminal device 200. The identified spectrum information is transmitted to the illumination device 300 via the second communication interface 107.

The controller 301 of the illumination device 300 controls the light source unit 302 and the spectrum adjusting unit 303 based on the spectrum information received from the information processing device 100. In the following, as an example, a case where the illumination device 300 can individually adjust the intensities of the red, green, and blue lights included in the illumination light will be described. The intensities of the red, green, and blue light of the illumination light before adjusting the spectrum are Rd, Gd, and Bd, respectively, and the intensities of the red, green, and blue light after adjusting the spectrum are Ra, Ga, and Ba, respectively. Then, the spectrum of the illumination light is adjusted so that the intensities Ra, Ga, and Ba satisfy the following formula 5.

$$Ra = Rd \times F \times Rm$$

$$Ga = Gd \times F \times Gm$$

$$Ba = Bd \times Bm/B \text{ max}$$

In the spectrum adjusting process represented by the formula 5, the intensity Bd of the illumination light before adjusting of the spectrum is multiplied by the ratio of the measured value Bm of the blue component to the maximum value Bmax. For example, when the user has a high sensitivity to blue light (in other words, when the user has Irlen syndrome), by changing the intensity of the blue light from the intensity Bd to the intensity Ba, the intensity of blue light becomes smaller. As a result, the glare that the user feels with respect to the illumination light can be reduced.

Further, in the spectrum adjusting process represented by the formula 5, the intensity Rd of the illumination light before adjusting of the spectrum is multiplied by the ratio F and the measured value Rm, and the intensity Gd of the illumination light before the adjusting is multiplied by the ratio F and the measured value Gm. The ratio F represents the ratio of the visual sensitivity of the user to the red and green light to the visual sensitivity to the blue light. Further, the measured value Rm and the measured value Gm represent the visual sensitivity of the user to the red light and the visual sensitivity to the green light, respectively. Therefore, by this spectrum adjusting process, the color of the illumination light is adjusted in accordance with the disparity between the sensitivities of the user to the red, green, and blue lights.

As described above, in the present embodiment, the spectrum of the illumination light is adjusted according to the color vision characteristics of the user, and thereby it is possible to provide to the user a space illuminated by illumination light that makes it easy for users to identify colors without feeling dazzled. Space can be provided to users. Further, according to the present disclosures, when the illumination device 300 is a display device such as a television, a personal computer, or a tablet terminal, the display device can display a screen on which colors can be easily identified without the user feeling dazzled.

Further, in the present embodiment, the mobile terminal device 200 and the information processing device 100 are set in advance so that the communication is automatically established. Therefore, the spectrum of the illumination light can be adjusted to have a spectrum suitable for the user's color vision characteristics without the user operation of the illumination device 300.

In the present embodiment, the spectrum of the illumination light is adjusted based on the color vision characteristics of the user measured in advance. Therefore, in the present embodiment, it is possible to prevent the spectrum of the illumination light from changing each time the adjusting is made, as compared with the case where the user manually adjusts the spectrum of the illumination light. Further, when the information processing device 100 and the illumination device 300 according to the present embodiment are installed in each of a plurality of rooms, the illumination light in each room is adjusted based on the same color vision characteristics. Therefore, in the plurality of illumination devices 300, it is possible to align the spectrum of the illumination light with a value suitable for the color vision characteristics of the user.

First Modification of First Embodiment

In the first embodiment, the color vision information of the user is recorded in the mobile terminal device 200, but the embodiment of the present disclosures is not limited to this configuration. For example, the color vision information of the user may be recorded in the storage 105 of the information processing device 100 together with user information which identifies the user of the mobile terminal device 200. In this case, the user information identifying the user is transmitted from the mobile terminal device 200 to the information processing device 100. The information processing device 100 identifies the user of the mobile terminal device 200 based on the received user information and extracts the color vision information of the user from the storage 105. Next, the information processing device 100 identifies the spectrum information corresponding to the color vision information of the user and transmits it to the illumination device 300. According to this configuration, since it is not necessary to store the color vision information of the user in the mobile terminal device 200, for example, even when the user changes the mobile terminal device 200 to be used, it is possible to provide an illumination environment suitable for the color vision characteristics of the user.

Further, in the first embodiment, the spectrum information according to the color vision characteristics of the user is recorded in the storage 105 of the information processing device 100, but the embodiment of the present invention is not limited to this configuration.

The spectrum information may be recorded in the storage 205 of the mobile terminal device 200. In this case, spectrum information is transmitted from the mobile terminal device 200 to the information processing device 100. The information processing device 100 transmits the spectrum information received from the information processing device 100 to the illumination device 300.

Second Modification of First Embodiment

Information transmitted from the mobile terminal device 200 to the information processing device 100 is not limited to the color vision information indicating the color vision characteristics of the user. For example, when the user has the color blindness or the color weakness and wears glasses or contact lenses for correcting the color blindness or the color weakness, information indicating the characteristics of the glasses or contact lenses may be transmitted to the information processing device 100 with the color vision information. In this case, the spectrum of the illumination light is adjusted in consideration of the characteristics of the glasses and contact lenses in addition to the spectrum information.

According to this modification, even though the color vision characteristics of the user are corrected by the glasses or contact lenses, it is possible to prevent the spectrum of the illumination light from being further adjusted (in other words, from being excessively adjusted). In addition, when the user wears the glasses or contact lenses for correcting the color vision characteristics, the intensity of the illumination light that the user sees is usually smaller than when the user does not wear the glasses or contact lenses. In this case, the user may feel that the room is dark due to the low brightness of the illumination light. Therefore, when the user wears the glasses or contact lenses, the illumination light may be adjusted such that the brightness is increased. As a result, the color vision characteristics of the user can be corrected, and the user's feeling of darkness can be reduced. Further, when the user wears the glasses for correcting the color blindness or color weakness, the spectrum of the illumination light may not be adjusted.

Third Modification of First Embodiment

In the first embodiment, the illumination light adjusting system 1 includes a single illumination device 300, but the embodiment of the present invention is not limited to this configuration. For example, the illumination light adjusting system may include a plurality of illumination devices.

FIG. 10 shows a schematic view of the illumination light adjusting system 11 according to a third modification of the first embodiment. The illumination light adjusting system 11 of this modification includes an information processing device 100, a mobile terminal device 200, and two illumination devices 1300 and 2300. The illumination device 1300 is a lighting fixture. The illumination device 2300 has an information processing terminal 2310 and a display device 2320 connected to the information processing terminal 2310.

The configurations of the information processing device 100, the mobile terminal device 200, and the illumination device 1300 are the same as those of the information processing device 100, the mobile terminal device 200, and the illumination device 300 of the first embodiment. In this modification, the illumination device 1300 can communicate with the illumination device 2300 via a communication interface 304.

The information processing terminal 2310 of the illumination device 2300 includes a CPU 2311, a RAM 2312, a ROM 2313, a program 2314, a storage 2315, a communication interface 2316, and an interface 2317. The display device 2320 of the illumination device 2300 is, for example, a liquid crystal display. The display device 2320 includes a controller 2321, a display unit 2322, and an interface 2323. The display unit 2322 includes a light source unit 2322a and a spectrum adjusting unit 2322b. The light source unit 2322a includes a light source and a light guide plate which guides the illumination light emitted from the light source. The spectrum adjusting unit 2322b includes a spatial light modulation element and a color filter which modulates the illumination light emitted from the light source unit 2322a. The controller 2321 controls the display unit 2322 based on a video signal received from a personal computer via the interface 2323, and causes the display unit 2322 to display the video.

In this modification, the illumination device 1300 and the illumination device 2300 are installed in the same room. When communication between the mobile terminal device 200 and the information processing device 100 is established and the color vision information of the user is transmitted from the mobile terminal device 200 to the information processing device 100, the information processing device 100 transmits the spectrum information corresponding to the received color vision information to the illumination device 2300. Upon receiving the spectrum information, the information processing terminal 2310 of the illumination device 2300 determines whether the display device 2320 is lit on or off When it is determined that the display device 2320 is lit on, the information processing terminal 2310 adjust the video signal to be transmitted to the display device 2320 based on the spectrum information. The display device 2320 displays the video (or an image) based on the video signal. As this video signal, an RGB image signal representing each color component in an RGB color space, a luminance signal Y, a color difference signal Cb, Cr, or the like is used according to specifications of the display device 2320. Any type of the video signal can be converted into the RGB image signal by performing a matrix conversion process. When it is determined that the display is lit on, the RGB image signal is adjusted.

Assuming that levels of the RGB image signals of the display before adjusting the spectrum are Rs1, Gs1, and Bs1, respectively, and levels of the RGB image signals after adjusting the spectrum are Rs2, Gs2, and Bs2, respectively, the image signals Rs2, Gs2, and Bs2 are represented by the following formula 6.

$$Rs2 = Rs1 \times F \times Rm$$

$$Gs2 = Gs1 \times F \times Gm$$

$$Bs2 = Bs1 \times Bm/B\ \max \qquad \text{(Formula 6)}$$

By adjusting the RGB image signals in accordance with the formula 6, it is possible to display, on the display device 2320, a video of which the user can easily recognize color without feeling dazzled.

In formula 6, the image signals Rs1, Gs1 and Bs1 are adjusted, but the adjusting process of the image signals according to the present disclosures is not limited to the process. For example, by applying the matrix conversion to formula 6, the image signals YCbCr may be adjusted instead of the image signals RGB.

When it is determined that the display device 2320 is lit on, the information processing terminal 2310 transmits, to the illumination device 1300, a signal indicating that it is not necessary to adjust the spectrum of the illumination light emitted from the illumination device 1300. Alternatively, the information processing terminal 2310 does not transmit a signal to the illumination device 1300. Thus, the adjusting of the spectrum is not executed at the illumination device 1300.

On the other hand, when it is determined that the display device 2320 is lit off, the information processing device 2310 transmits the spectrum information, which is received from the information processing device 100, to the illumination device 1300. The illumination device 1300 adjusts the spectrum of the illumination light based on the spectrum information.

When there are a plurality of illumination devices whose spectra are adjustable in a single room, if the spectra of illumination light of all the illumination devices are adjusted based on the color vision information, the spectra of the illumination lights in the single room are excessively adjusted. For example, when the display device 2320 of the illumination device 2300 is illuminated by the illumination light of the illumination device 1300 if the spectra of the illumination lights of both the illumination devices 1300 and 2300 are adjusted, the image displayed on the display device 2320 may not be suitable for the user's color vision characteristics.

In this modification, when the spectrum of the illumination light is adjusted for one of the plurality of illumination devices, the spectra of the illumination lights of the other illumination devices are not adjusted. Therefore, it is possible to prevent the spectra of the illumination lights from being excessively adjusted. In this modification, for example, when the spectrum of the image of the display device 2320 is adjusted, the spectrum of the illumination light of the illumination device 1300 is not adjusted. As a result, the user can see an image having a spectrum suitable for his/her color vision characteristics on the display device 2320. Further, when the display device 2320 is turned off, only the spectrum of the illumination light of the illumination device 1300 is adjusted. As a result, the room in which the illumination device 1300 is installed becomes an illumination environment suitable for the color vision characteristics of the user.

In the present modification, when the display device 2320 is lit on, the information processing terminal 2310 transmits the information indicating that the spectrum adjustment is not necessary to the illumination device 1300, but the embodiment of the present disclosures is not limited to the configuration. The information processing device 100 may determine which of the plurality of illumination devices that the illumination spectrum is to be adjusted based on an operating state of each illumination device. For example, when the information processing device 100 establishes communication with the information processing terminal 2310 and receives state information indicating that the display device 2320 is on or off, the information processing device 100 determines the illumination device of which the spectrum is to be adjusted based on the state information. Then, the information processing device 100 transmits a signal instructing the spectrum adjustment or a signal indicating that the spectrum adjustment is not necessary to each illumination device.

Further, the user may input, to the mobile terminal device 200, the illumination device information indicating which of the plurality of illumination devices the spectrum of the illumination device is to be adjusted. In this case, the mobile terminal device 200 transmits the illumination device information to the information processing device 100. The information processing device 100 transmits the spectrum information only to the illumination device indicated by the illumination device information.

Further, in the third modification, the spectrum of the illumination light is adjusted for only one of the plurality of illumination devices, but the embodiment of the present disclosures is not limited to this. For example, the illumination light adjusting system 11 may adjust the spectrum of illumination light for the plurality of illumination devices, and superimposes the plurality of illumination lights whose spectra have been adjusted to generate illumination light having a spectrum suitable for the color vision characteristics of the user.

Second Embodiment

In the first embodiment, the color vision information of the user of the mobile terminal device 200 or the user information for identifying the user is transmitted from the mobile terminal device 200 to the information processing device 100, but the embodiment of the present invention is not limited to this configuration.

FIG. 11 shows a schematic view of the illumination light adjusting system 21 according to the second embodiment of the present invention. The illumination light adjusting system 21 of the present embodiment includes the information processing device 100, the illumination device 300, and an imaging device 400. Since the configurations of the information processing device 100 and the illumination device 300 are the same as those of the information processing device 100 and the illumination device 300 of the first embodiment, detailed explanation thereof will be omitted.

The imaging device 400 includes a controller 401, an imaging unit 402, a storage 403, and a communication interface 404. The imaging unit 402 is controlled by the controller 401 and is used to take an image of the user and generate image data of the image. The storage 403 stores information such as the image taken by the imaging unit 402. The communication interface 404 is used for wireless or wired communication with the information processing device 100.

The imaging device 400 is installed in the room where the information processing device 100 and the illumination device 300 are installed, or at the entrance of the room, and used for face recognition of the user who uses the room.

Upon the user using the imaging device 400 for taking an image of a face of the user, the imaging device 400 identifies the user based on the captured image of the user's face. For example, the storage 403 of the imaging device 400 records face information indicating facial features of the user. The imaging device 400 extracts a human face from the captured image and determines whether or not the extracted facial features match the recorded facial features (i.e., the face information) of the user. When it is determined that the extracted facial features match the recorded face information, the imaging device 400 identifies the user of which the image is taken as a user corresponding to the recorded face information. Then, the imaging device 400 transmits the user information indicating the identified user to the information processing device 100. The imaging device 400 may include a digital camera or a video camera. Further, the imaging device 400 may include a circuit configured to identify the user or the user's face and extract the facial features.

The storage 105 of the information processing device 100 stores the color vision information of the user with the user information identifying the user. When the information processing device 100 receives the user information from the imaging device 400, the information processing device 100 identifies the user whose face has been taken based on the user information, and extracts the color vision information of the user from the storage 105. Next, the information processing device 100 identifies the spectrum information corresponding to the color vision information of the user and transmits it to the illumination device 300. It is noted that the information processing device 100 may identify the spectrum information according to the color vision characteristics of the user based on the received user information without using the color vision information.

The controller 301 of the illumination device 300 controls the light source unit 302 and the spectrum adjusting unit 303 based on the spectrum information received from the information processing device 100. As a result, the spectrum of the illumination light is adjusted according to the color vision characteristics of the user.

According to the present embodiment, the user is identified by the imaging device 400, and the spectrum of the illumination light is adjusted according to the color vision characteristics of the identified user. Therefore, the user does not need to have a mobile terminal device that stores the user information for identifying himself/herself or his/her own color vision information.

First Modification of Second Embodiment

In the second embodiment, the user is identified by using the image taken by the imaging device 400, but the embodiment of the present disclosures is not limited to this configuration. For example, based on the image taken by the imaging device 400, it may be determined, with the user, whether or not the user wears glasses for correcting color vision characteristics. In this case, the spectrum and brightness of the illumination light are adjusted according to the color vision characteristics of the user and the characteristics of the glasses.

Second Modification of Second Embodiment

In the second embodiment, the user is identified by using the imaging device 400, but the embodiment of the present disclosures is not limited to this configuration. For example, the information processing device 100 may have a user interface configured to receive information input by the user. In this case, the storage 105 of the information processing device 100 stores the identification information for identifying the user. The information processing device 100 identifies the user by comparing the information received via the user interface with the identification information stored in the storage 105.

Further, the information processing device 100 may identify the user by using a device configured to detect biometric information such as a user's voice, a fingerprint or the like. In this case, information indicating the biometric information of the user is stored in the storage 105 of the information processing device 100. Further, the information processing device 100 includes a detection device configured to detect the biometric information of the user instead of the imaging device 400. The information processing device 100 configured to identify the user by comparing the biometric information detected by the detection device with the biometric information stored in the storage 105.

Third Embodiment

In the first and second embodiments, the spectrum information is transmitted from the information processing device 100 to the illumination device 300, but the embodiment of the present disclosures is not limited to these configurations. The spectrum information may be transmitted from the mobile terminal device 200 to the illumination device 300 without through the information processing device 100.

FIG. 12 shows a schematic view of the illumination light adjusting system 31 according to the third embodiment of the present disclosures. The configuration of the illumination light adjusting system 31 of the present embodiment is the same as that of the first embodiment except that the information processing device 100 is not provided. The mobile terminal device 200 and the illumination device 300 can communicate with each other via the communication interface 208 and the communication interface 304.

In the present embodiment, the storage 205 of the mobile terminal device 200 stores the spectrum information according to the color vision characteristics of the user. When the user having the mobile terminal device 200 enters the room in which the illumination device 300 is installed, communication between the mobile terminal device 200 and the illumination device 300 is established. When the communication is established between the mobile terminal device 200 and the illumination device 300, the mobile terminal device 200 reads out the spectrum information corresponding to the color vision characteristics of the user stored in the storage 205. The read spectrum information is transmitted to the illumination device 300.

The controller 301 of the illumination device 300 controls the light source unit 302 and the spectrum adjusting unit 303 based on the spectrum information received from the mobile terminal device 200.

According to this embodiment, the spectrum information is transmitted from the mobile terminal device 200 to the illumination device 300 without through an information processing device. Therefore, it is not necessary to install an information processing device in the room, and the illumination light adjusting system 31 can be simplified and reduced in cost.

In the present embodiment, the information transmitted from the mobile terminal device 200 to the illumination device 300 may be the color vision information of the user instead of the spectrum information. In this case, the illumination device 300 determines how to adjust the spectrum of the illumination light based on the received color vision information.

Fourth Embodiment

In the above-described embodiment, the case where the illumination device is a device having a light source of the illumination light such as a lighting fixture or a display has been described, but the embodiment of the present disclosures is not limited to this configuration. For example, the illumination device may have no light source and may be capable of changing the spectrum of transmitted illuminating light.

FIG. 13 shows an illumination light adjusting system 41 according to a fourth embodiment of the present invention. The illumination light adjusting system 41 of the present embodiment includes a mobile terminal device 200 and an illumination device 3300. Since the configuration of the mobile terminal device 200 is the same as that of the above-described embodiment, detailed description thereof will be omitted.

The illumination device 3300 includes a controller 3301, a variable filter unit 3302, and a communication interface 3303. The variable filter unit 3302 can change the spectrum of the transmitted illumination light. The controller 3301 controls an operation of the variable filter unit 3302. The communication interface 3303 is used for wired or wireless communication with the mobile terminal device 200. The illumination device 3300 of the present embodiment does not have a light source and adjusts the spectrum of light incident from outside.

FIG. 14A shows an external view of the illumination device 3300, and FIG. 14B is a schematic view for explaining the structure of the variable filter unit 3302. The illumination device 3300 has a shape like glasses or a head-mounted display. The controller 3301 and the communication interface 3303 are built, for example, in an arm (i.e., a temple) portion of the glasses. The illumination device 3300 is attached to the user's face so that such the variable filter unit 3302 covers the user's eyes. The variable filter unit 3302 is divided into a plurality of pixels 30, and each pixel 30 has a polarizer 31, a liquid crystal panel 32, a color filter 33, and an analyzer 34. Further, each of the liquid crystal panel 32 and the color filter 33 is divided into three for each pixel 30. Color filters 33R, 33G, and 33B which is the color filter 33 divided into three are color filters that transmit only red, green, and blue lights, respectively. Further, the divided liquid crystal panels 32R, 32G, and 32B are arranged at positions corresponding to each color filter.

The illumination light incident on the illumination device 3300 from the outside becomes polarized light having a particular polarization direction by the polarizer 31 and is incident on the liquid crystal panel 32. The liquid crystal panel 32 can individually apply a driving voltage to each divided region. For example, the liquid crystal panel 32 has a TN-oriented liquid crystal layer and rotates the polarization direction of the transmitted light by 90 degrees in a state where the driving voltage is not applied. Further, the liquid crystal panel 32 does not rotate the polarization direction of the transmitted light when the driving voltage is applied.

The illumination light transmitted through the liquid crystal panel 32 is incident on the analyzer 34, and only the illumination light in the particular polarization direction passes through the analyzer 34. By controlling the voltage applied to each pixel 30 of the liquid crystal panel 32, the illumination device 3300 can switch whether or not to rotate the polarization direction of the light transmitted through each color filter 33. Thereby, the spectrum of the light transmitted through the analyzer 34 can be changed.

In the present embodiment, the storage 205 of the mobile terminal device 200 stores the spectrum information according to the color vision characteristics of the user. When the communication between the mobile terminal device 200 and the illumination device 3300 is established, the mobile terminal device 200 reads out the spectrum information corresponding to the color vision characteristics of the user stored in the storage 205. The read spectrum information is transmitted to the illumination device 3300.

The controller of the illumination device 3300 controls the variable filter unit 3302 based on the spectrum information received from the mobile terminal device 200. As a result, an external light (i.e., the illumination light) transmitted through the illumination device 3300 is adjusted to a spectrum suitable for the color vision characteristics of the user.

According to the present embodiment, even when the illumination device 3300 does not have a light source of the illuminating light, an illumination environment suitable for the color vision characteristics of the user can be provided by adjusting the spectrum of external light.

The above is the description of the exemplary embodiments of the present disclosures. The embodiments of the present disclosures are not limited to those described above, and various modifications can be made within a scope of a technical idea of the present disclosures. For example, the embodiments of the present disclosures also include an appropriately combination of embodiments and obvious embodiments as exemplified in the specification.

What is claimed is:

1. An illumination light adjusting system comprising:
   a color vision characteristics storage configured to store color vision characteristics of a user, the color vision characteristics indicating a user-specific visual sensitivity;
   a wavelength characteristics changing unit configured to change wavelength characteristics of illumination light based on the color vision characteristics stored in the color vision characteristics storage; and
   at least one processor configured to:
     identify the user; and
     extract, from the color vision characteristics storage, the color vision characteristics of the identified user,
   wherein the wavelength characteristics changing unit is further configured to change the wavelength characteristics of the illumination light based on the extracted color vision characteristics.

2. The illumination light adjusting system according to claim 1, further comprising:
   a mobile terminal device configured to store identification information for identifying the user and communicate with the at least one processor,
   wherein at least one processor is further configured to identify the user based on the identification information received from the mobile terminal device.

3. The illumination light adjusting system according to claim 1, further comprising:
   an imaging unit configured to take an image of the user and generate image data of the image,
   wherein the at least one processor is configured to recognize a face of the user within the image, thereby identifying the user.

4. The illumination light adjusting system according to claim 1, further comprising:
   an information input unit configured to receive information input by the user,
   wherein the at least one processor is further configured to identify the user based on the information received by the information input unit.

5. The illumination light adjusting system according to claim 1,
   wherein the color vision characteristics storage is further configured to store information indicating a type and a degree of color vision deficiency of the user as the color vision characteristics.

6. The illumination light adjusting system according to claim 1,
   wherein the color vision characteristics storage is further configured to store a visual sensitivity of the user to light of a particular color as the color vision characteristics.

7. The illumination light adjusting system according to claim 6,
   wherein the wavelength characteristics changing unit is further configured to change an intensity of the light of the particular color included in the illumination light.

8. The illumination light adjusting system according to claim 1,
   wherein the color vision characteristics storage is further configured to store, as the color vision characteristics, at least one of a ratio and a difference between respective visual sensitivities of the user to light of a plurality of different colors.

9. The illumination light adjusting system according to claim 8,
   wherein the wavelength characteristics changing unit is further configured to change an intensity of light of at least one color of the plurality of different colors, included in the illumination light, based on the color vision characteristics.

10. The illumination light adjusting system according to claim 1, wherein the wavelength characteristics changing unit comprises:
    an optical filter configured to change wavelength characteristics of transmitted light or reflected light; and
    a controller configured to control the optical filter based on the color vision characteristics.

11. The illumination light adjusting system according to claim 1,
    wherein the wavelength characteristics changing unit comprises a light source unit configured to emit the illumination light.

12. The illumination light adjusting system according to claim 11,
    wherein the light source unit comprises a plurality of light sources having respective different emission wavelengths, and
    wherein the wavelength characteristics changing unit is further configured to change the wavelength characteristics of the illumination light by controlling the plurality of light sources individually.

13. An illumination light adjusting method comprising:
    storing color vision characteristics of a user, the color vision characteristics indicating a user-specific visual sensitivity;
    changing wavelength characteristics of illumination light based on the stored color vision characteristics;
    identifying the user;
    extracting the color vision characteristics of the identifying the user; and changing the wavelength characteristics of the illumination light based on the extracted color vision characteristics.

14. The illumination light adjusting method according to claim 13, further comprising:
communicating with a mobile terminal device storing identification information used to identify the user; and
identifying the user based on the identification information received from the mobile terminal device.

15. The illumination light adjusting method according to claim 13, further comprising:
taking an image of the user and generate image data of the image; and
recognizing a face of the user in the image to identify the user.

16. The illumination light adjusting method according to claim 13, further comprising:
receiving information input by the user,
identifying the user based on the input information.

17. The illumination light adjusting method according to claim 13, further comprising:
storing information indicating a type and degree of color vision deficiency of the user as the color vision characteristics.

18. The illumination light adjusting method according to claim 13, further comprising:
storing a visual sensitivity of the user for light in a particular color as the color vision characteristics.

19. The illumination light adjusting method according to claim 18, further comprising:
changing an intensity of the light of the particular color included in the illumination light.

20. The illumination light adjusting method according to claim 13, further comprising:
storing, as the color vision characteristics, at least one of a ratio and a difference between respective visual sensitivities of the user to light of a plurality of different colors.

21. The illumination light adjusting method according to claim 20, further comprising:
changing intensity of at least one color of the plurality of different colors based on the color vision characteristics.

22. The illumination light adjusting method according to claim 13, further comprising:
controlling an optical filter configured to change wavelength characteristics of transmitted light or reflected light based on the color vision characteristics.

23. The illumination light adjusting method according to claim 13, further comprising:
changing the wavelength characteristics of the illumination light by individually controlling a plurality of light sources having different emission wavelengths from each other.

24. A non-transitory computer-readable storage medium storing computer-readable instructions configured to, when executed by a computer, cause the computer to perform the illumination light adjusting method according to claim 13.

* * * * *